(12) United States Patent  
Koga et al.

(10) Patent No.: US 6,753,435 B1  
(45) Date of Patent: Jun. 22, 2004

(54) INTERMEDIATES FOR VITAMIN D AND PROCESSES FOR THE PREPARATION THEREOF

(75) Inventors: Masahiro Koga, Yamaguchi (JP); Toru Minoshima, Yamaguchi (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 10/239,778

(22) PCT Filed: Mar. 30, 2000

(86) PCT No.: PCT/JP00/02033

§ 371 (c)(1),  
(2), (4) Date: Sep. 25, 2002

(87) PCT Pub. No.: WO01/74764

PCT Pub. Date: Oct. 11, 2001

(51) Int. Cl.[7] .................... C07C 401/00; C07C 309/00  
(52) U.S. Cl. .......................................... 552/653; 558/54  
(58) Field of Search ............................. 552/653; 558/54

(56) References Cited

U.S. PATENT DOCUMENTS 5,089,641 A  *  2/1992  DeLuca et al. ............. 552/653  
5,250,523 A  * 10/1993  DeLuca et al. ............. 552/653  
5,932,565 A       8/1999  Grue-S.o slashed.rensen

FOREIGN PATENT DOCUMENTS

| JP | 63-208568 | * | 8/1988 |
| JP | 2-3695 |  | 1/1990 |
| JP | 2-3695 A |  | 1/1990 |
| WO | WO 97/37972 A1 |  | 10/1997 |
| WO | WO 99/61417 | * | 12/1999 |

OTHER PUBLICATIONS

Mercedes Torneiro, et al., "An Efficient Route to 1α, 25–Dihydroxyvitamin $D_3$ Functionalized at C–11," Tetrahedron Letters, 1992, pp. 105–108, vol. 33, No. 1, Pergamon Press, Great Britain.

(List continued on next page.)

*Primary Examiner*—Barbara P. Badio  
(74) *Attorney, Agent, or Firm*—Sughrue Mion, PLLC

(57) ABSTRACT

An object of the present invention is to provide intermediates for the synthesis of 1α-hydroxyvitamin D derivatives useful as drugs and processes for the preparation thereof.

Namely, the present invention is a process for the preparation of a compound represented by the formula (2), which comprises reacting a compound represented by the formula (1) with a compound represented by the formula (4) in the presence of a palladium catalyst, a process for the preparation of a compound represented by the formula (3), which comprises further catalytically reducing the resulting compound represented by the formula (2) in the presence of a Lindlar catalyst and hydrogen gas and heating the obtained product and a process for the preparation of a compound represented by the formula (5), which comprises further oxidizing the resulting compound represented by the formula (3) with an oxidizing agent and the compounds represented by the formulae (1) to (3):

(1)

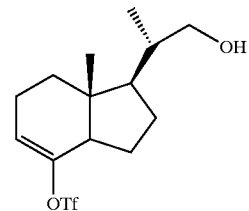

(4)

(2)

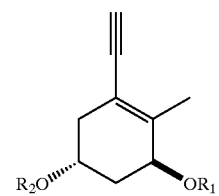

(3)

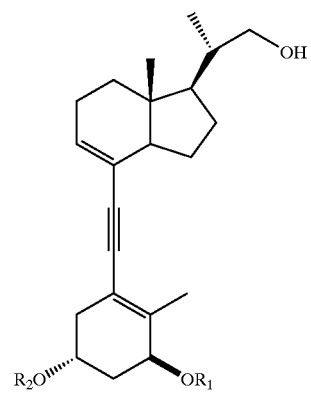

(5)

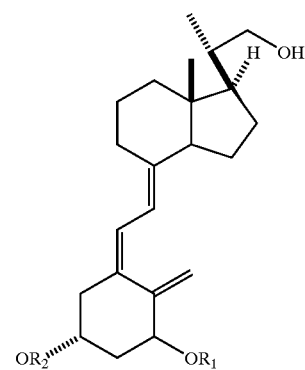

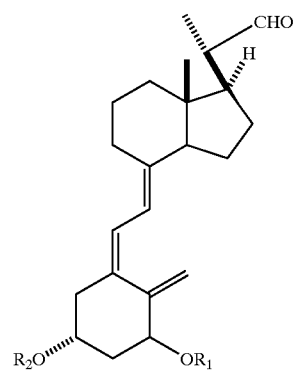

4 Claims, No Drawings

OTHER PUBLICATIONS

L. Castedo, et al., "Palladium–Catalyzed Synthesis of Dienynes Related to 1α, 25–Dihydroxyvitamin $D_3$," Tetrahedron Letters, 1988, pp. 1203–1206, vol. 29, No. 10, Pergamon Press, Great Britain.

Jose L. Mascarenas, et al., Palladium–Catalysed Coupling of Vinyl Triflates with Enynes and its Application to the Synthesis of 1α, 25–Dihydroxyvitamin $D_3^{1,2}$, Tetrahedron, 1991, pp. 3485–3498, vol. 47, No. 20/21, Pergamon Press, Great Britain.

Michael L. Curtin, "1 α, 25–Dihydroxyprevitamin $D_3$: Synthesis of the 9, 14, 19, 19, 19–Pentadeuterio Derivative and a Kinetic Study of Its [1–7]–Sigmatropic Shift to 1 α, 25–Dihydroxyvitamin $D_3^1$," J. Am. Chem. Soc., 1991, pp. 6958–6966, vol. 113, No. 18.

William J. Scott, et al., "Palladium–Catalyzed Olefination of Vinyl Triflates," J. Org. Chem., 1985, pp. 2302–2308, vol. 50, No. 13.

F. Javier Sardina, et al., "Studies on the Synthesis of Side–Chain Hydroxylated Metabolites of Vitamin D. 2. Stereocontrolled Synthesis of 25–Hydroxyvitamin $D_2^1$," J. Org. Chem., 1986, pp. 1264–1269, vol. 51, No. 8.

William H. Okamura, et al., "Synthesis and Biological Activity of 9, 11–Dehydrovitamin $D_3$ Analogues: Stereoselective Preparation of 6β–Vitamin D Vinylallenes and a Concise Enynol Synthesis for Preparing the A–Ring[1-a-c]," J. Org. Chem., 1989, pp. 4072–4083, vol. 54, No. 17.

Shin Jikken Kagaku Koza, "Oxidation and Reduction," J. Chem. Soc., 1971, pp. 425–427, vol. 15, 2963.

T.M. Dawson, "Calciferol and its Relatives. Part XVI. Total Synthesis of Precalciferol$_3$," J. Chem. Soc., 1971, pp. 2960–2966.

Shin Jikken Kagaku Koza, "Oxidation and Reduction" J. Org. Chem., 1978, pp. 802–829, vol. 44, 4148.

Anthony J. Mancouso, "Structure of Dimethyl Sulfoxide–Oxalyl Chloride Reaction Product. Oxidations of Heteroaromatic and Diverse Alcohols to Carbonyl Compounds," J. Org. Chem., 1979, pp. 4148–4150, vol. 44, No. 23.

Anthony J. Mancouso, "Oxidation of Long–Chain and Related Alcohols to Carbonyls by Dimethyl Sulfoxide "Activated" by Oxalyl Chloride," J. Org. Chem., 1978, pp. 2480–2482, vol. 43, No. 12.

S.L. Huang, et al., "Further Studies on the Oxidation of Alcohols to Carbonyl Compounds by Dimethyl Sulfoxide/ Trifluoroacetic Anhydride," Communications, 1978, pp. 297–299, vol. 78, Georg Theime Publishers.

* cited by examiner

INTERMEDIATES FOR VITAMIN D AND PROCESSES FOR THE PREPARATION THEREOF

This application is a 371 of PCT/JP00/02033 filed Mar. 30, 2000.

TECHNICAL FIELD

The present invention relates to intermediates for the synthesis of vitamin D derivatives useful as drugs and processes for the preparation of the same. More particularly it relates to intermediates for the synthesis of 1α-hydroxyvitamin D derivatives useful as drugs such as osteogenesis promoters, tumorous cell growth inhibitors, immunosuppressants, anti-hypercalcemia drugs, therapeutic agents for inflammatory respiratory diseases and the like and processes for the preparation of the same.

BACKGROUND ART

It has hitherto been disclosed that vitamin D compounds and metabolites thereof play a highly important role as control substances of metabolism of in vivo calcium or phosphates in patent publications and general literature. Processes according to JP-B (hereinafter JP-B refers to Japanese Examined Patent Publication) No. 2-24268 and Tetrahedron Letters, 1992, 33, 105 are known as processes for the preparation of the vitamin D compounds.

Robert Henry Hesse et al. disclose processes for the preparation of vitamin D derivatives represented by the formula (5) from vitamin $D_2$ in nine steps:

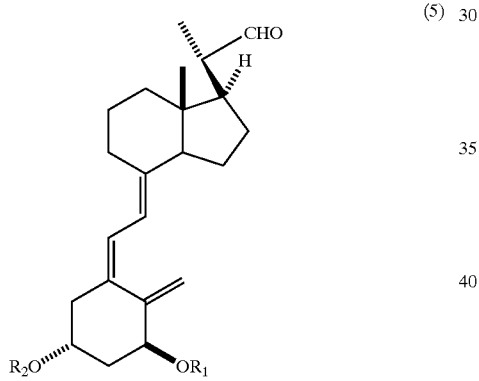
(5)

(JP-B No. 2-24268); however, it may be scarcely said that the processes are industrial processes for the preparation because toxic selenium dioxide ($SeO_2$) is used in steps of introducing a hydroxy group in the course of the processes.

$VD_2 \longrightarrow$

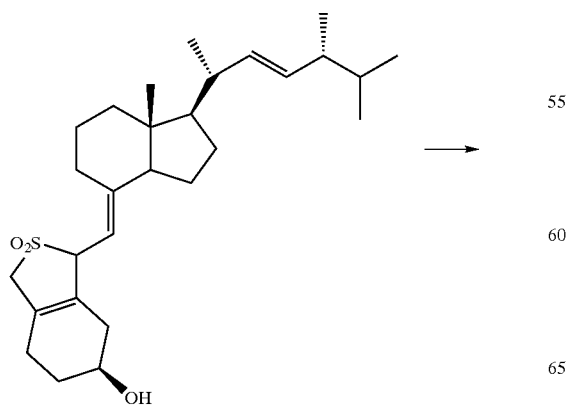

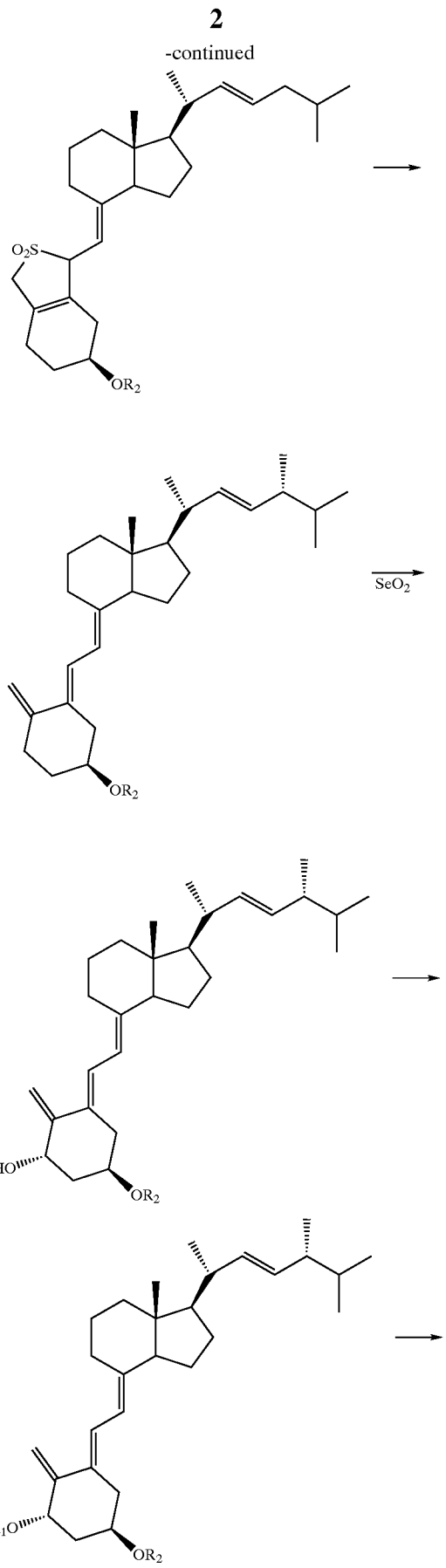

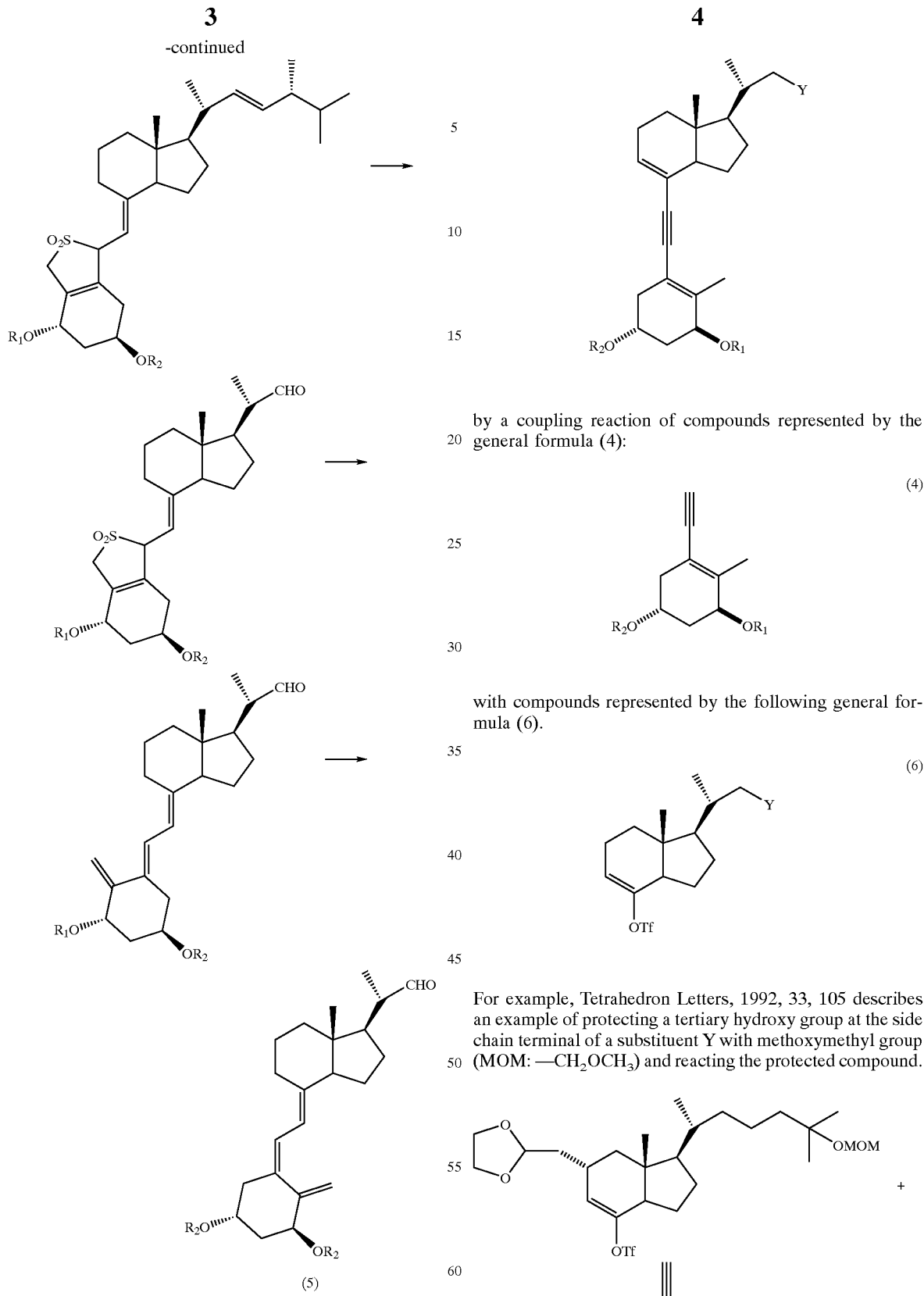

by a coupling reaction of compounds represented by the general formula (4):

(4)

with compounds represented by the following general formula (6).

(6)

For example, Tetrahedron Letters, 1992, 33, 105 describes an example of protecting a tertiary hydroxy group at the side chain terminal of a substituent Y with methoxymethyl group (MOM: —CH$_2$OCH$_3$) and reacting the protected compound.

On the other hand, Mercedes Torneiro, L. Castedo, W. H. Okamura et al. disclose processes for the preparation of vitamin D derivatives represented by the formula:

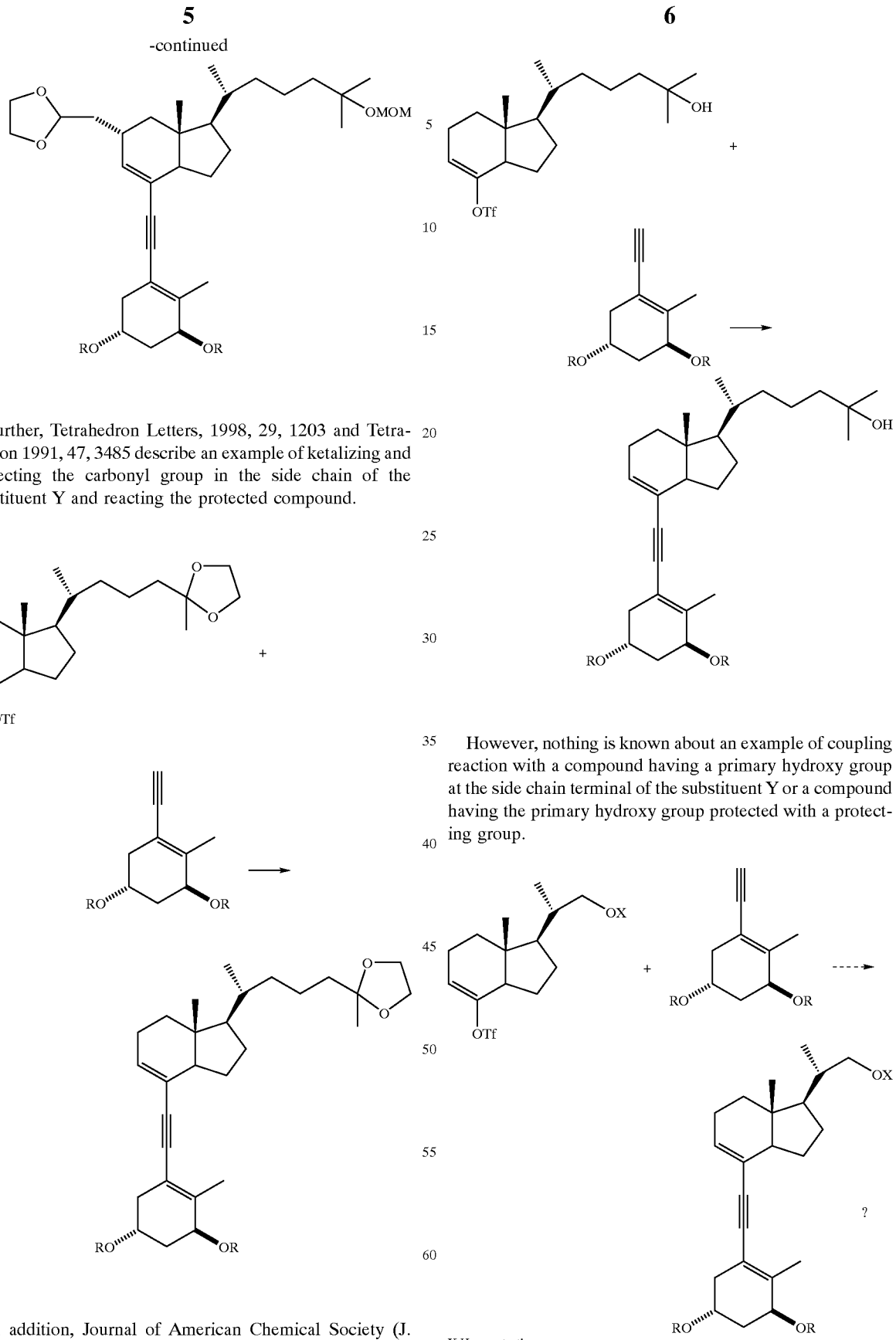

Further, Tetrahedron Letters, 1998, 29, 1203 and Tetrahedron 1991, 47, 3485 describe an example of ketalizing and protecting the carbonyl group in the side chain of the substituent Y and reacting the protected compound.

In addition, Journal of American Chemical Society (J. Am. Chem. Soc.), 1991, 113, 6958 describes an example of reaction with a compound having a tertiary hydroxy group at the side chain terminal of the substituent Y.

However, nothing is known about an example of coupling reaction with a compound having a primary hydroxy group at the side chain terminal of the substituent Y or a compound having the primary hydroxy group protected with a protecting group.

X:H or protecting group of hydroxy group

By the way, coupling reaction of an acetylene compound with a triflate derivative (R-OTf) is known as the Stille reaction [for example, Stille et al., Journal of Organic Chemistry (J. Org. Chem.), 1985, 50, 2302]. The reaction is carried out by heating the acetylene compound and the triflate derivative in the presence of a palladium catalyst [Pd(0) or Pd(II)] and an additive [for example, triethylamine or lithium chloride (LiCl)] in a solvent (for example, tetrahydrofuran, ethanol, dimethylformamide or dimethyl sulfoxide) to prepare the objective coupling product.

An example of preparing vitamin $D_3$ derivatives utilizing the reaction conditions has been reported by Okamura et al. [for example, Journal of American Chemical Society (J. Am. Chem. Soc.), 1991, 113, 6958].

DISCLOSURE OF THE INVENTION

Accordingly, an object of the present invention is to provide novel intermediates for the synthesis of 1α-hydroxyvitamin D derivatives.

Another object of the present invention is to provide novel processes for the preparation of intermediates for the synthesis of the 1α-hydroxyvitamin D derivatives.

As a result of intensive studies made on the objects, the inventors have achieved the following invention. Namely, the present invention is a process for the preparation of a compound represented by the formula (2):

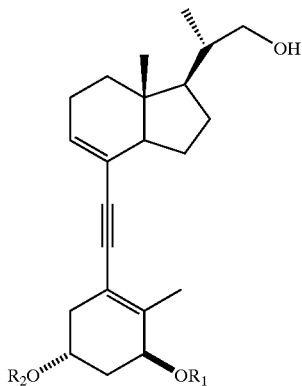

(2)

wherein, $R_1$ and $R_2$ are each the same as in the formula (4), which comprises reacting a compound represented by the formula (1):

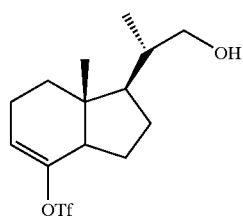

(1)

wherein, Tf represents $SO_2CF_3$, with a compound represented by the formula (4):

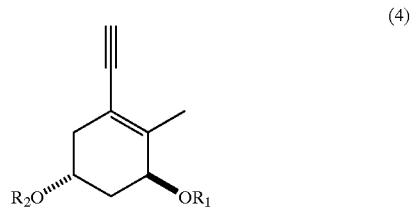

(4)

wherein, $R_1$ and $R_2$ are each the same or different and represent each a hydrogen atom, a tri($C_1$–$C_7$ hydrocarbon)silyl group, a diphenyl($C_{1-C7}$ hydrocarbon)silyl group or a group forming an acetal bond or an ester bond with an oxygen atom to which each of $R_1$ and $R_2$ is bound, in the presence of a palladium catalyst and an additive.

In addition, the present invention is a process for the preparation of a compound represented by the formula (3):

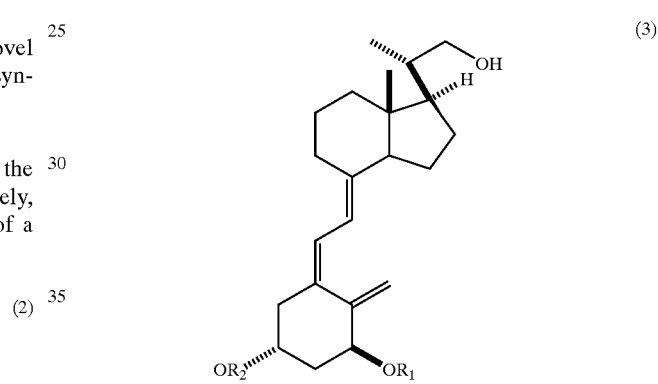

(3)

wherein, $R_1$ and $R_2$ are each the same as in the above formula (4), which comprises, if necessary, adding a basic compound in order to lower the activity of a Lindlar catalyst in the presence of the Lindlar catalyst and hydrogen gas, then catalytically reducing the compound represented by the formula (2):

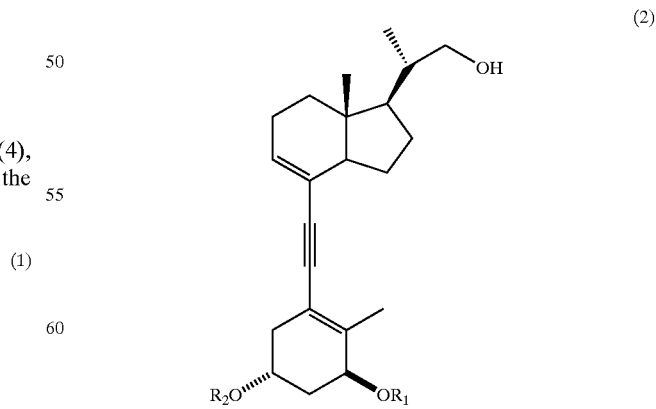

(2)

wherein, $R_1$ and $R_2$ are each the same as in the above formula (4), and further heating the obtained product.

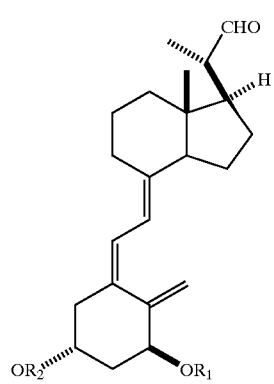

wherein, $R_1$ and $R_2$ are each the same as in the above formula (4), which comprises oxidizing the compound represented by the formula (3):

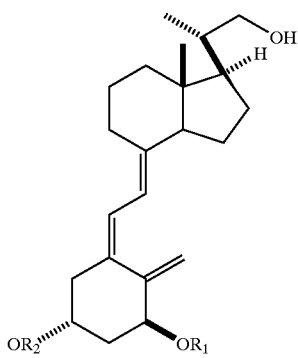

wherein, $R_1$ and $R_2$ are each the same as in the formula (4), with an oxidizing agent.

In addition, the present invention is the compound represented by the formula (1):

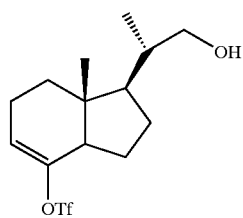

wherein, Tf represents $SO_2CF_3$, the compound represented by the formula (2):

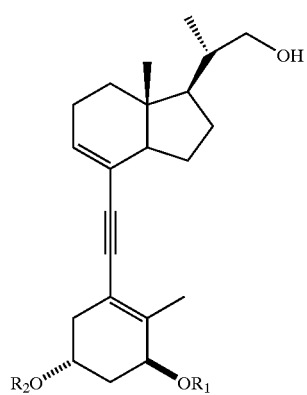

wherein, $R_1$ and $R_2$ are each the same as in the above formula (4) and the compound represented by the formula (3):

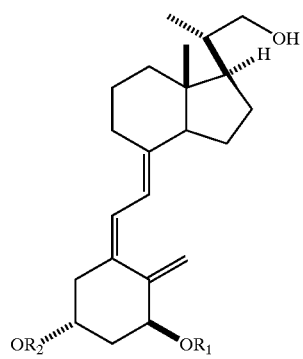

wherein, $R_1$ and $R_2$ are each the same as in the above formula (4), which are the intermediates for the synthesis of the vitamin D derivatives used in the processes for the preparation mentioned above.

BEST MODE FOR CARRYING OUT THE INVENTION

The compound which is represented by the formula (1) and used as a raw material in the processes of the present invention is prepared from vitamin $D_2$ through the following synthetic route:

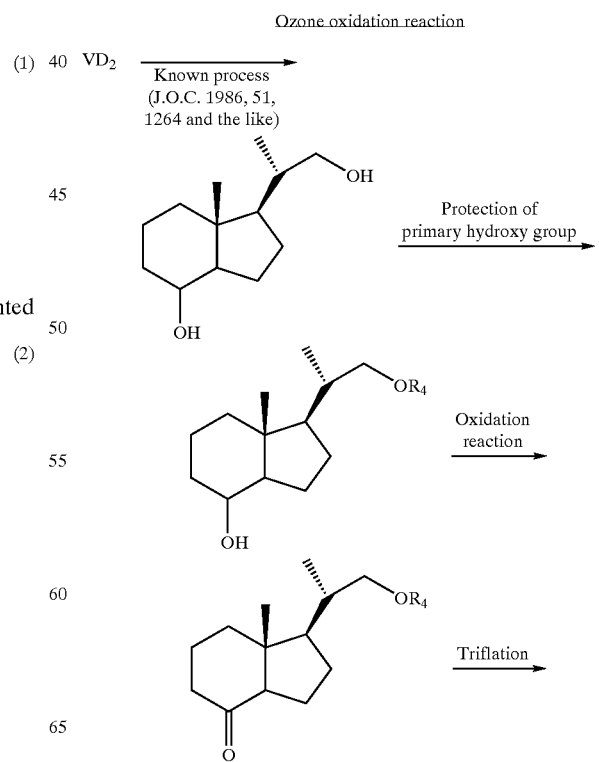

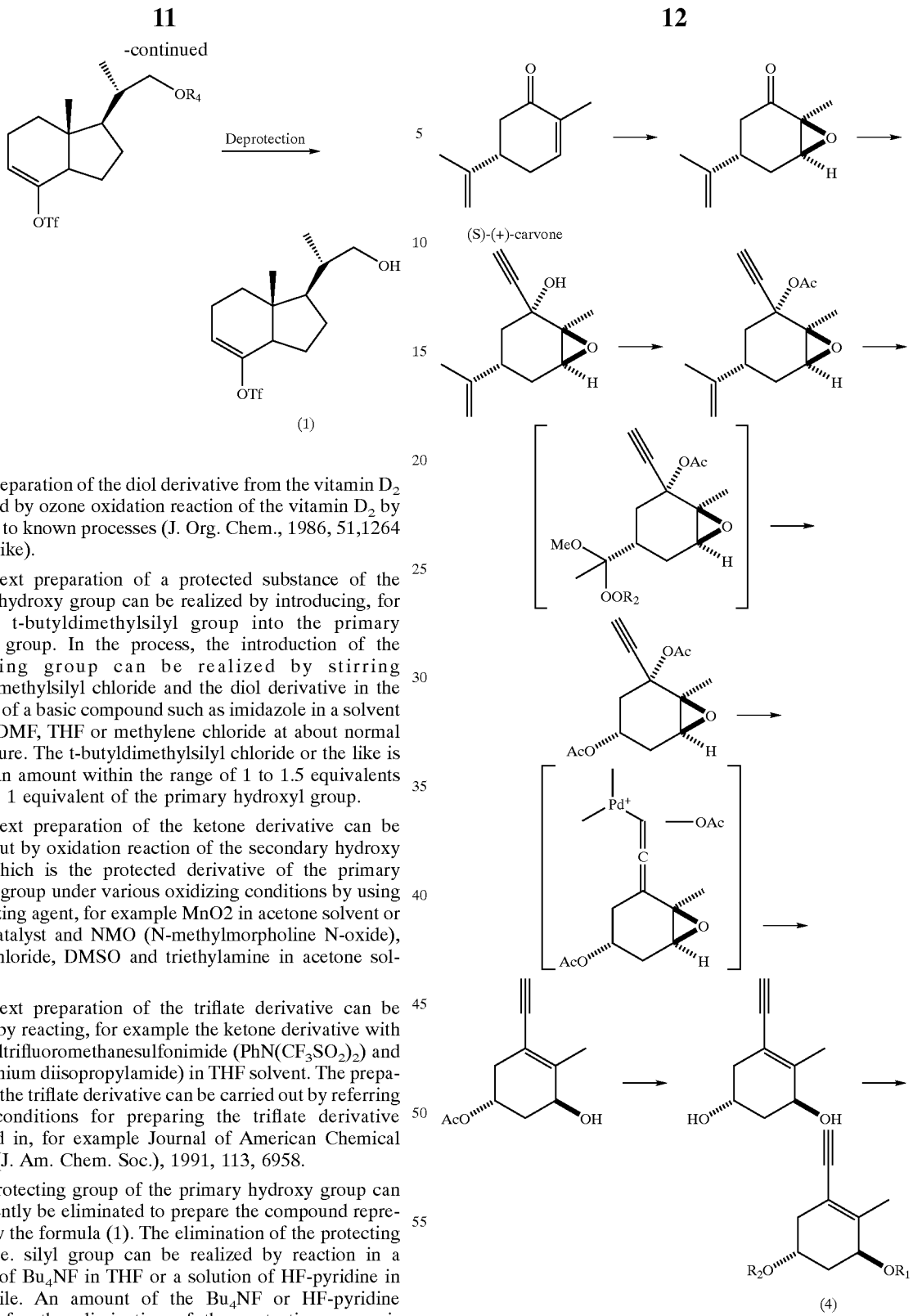

(4)

The preparation of the diol derivative from the vitamin $D_2$ is realized by ozone oxidation reaction of the vitamin $D_2$ by referring to known processes (J. Org. Chem., 1986, 51,1264 and the like).

The next preparation of a protected substance of the primary hydroxy group can be realized by introducing, for example t-butyldimethylsilyl group into the primary hydroxy group. In the process, the introduction of the protecting group can be realized by stirring t-butyldimethylsilyl chloride and the diol derivative in the presence of a basic compound such as imidazole in a solvent such as DMF, THF or methylene chloride at about normal temperature. The t-butyldimethylsilyl chloride or the like is used in an amount within the range of 1 to 1.5 equivalents based on 1 equivalent of the primary hydroxyl group.

The next preparation of the ketone derivative can be carried out by oxidation reaction of the secondary hydroxy group which is the protected derivative of the primary hydroxy group under various oxidizing conditions by using an oxidizing agent, for example $MnO2$ in acetone solvent or an Ru catalyst and NMO (N-methylmorpholine N-oxide), oxalyl chloride, DMSO and triethylamine in acetone solvent.

The next preparation of the triflate derivative can be realized by reacting, for example the ketone derivative with N-phenyltrifluoromethanesulfonimide ($PhN(CF_3SO_2)_2$) and LDA (lithium diisopropylamide) in THF solvent. The preparation of the triflate derivative can be carried out by referring to the conditions for preparing the triflate derivative described in, for example Journal of American Chemical Society (J. Am. Chem. Soc.), 1991, 113, 6958.

The protecting group of the primary hydroxy group can subsequently be eliminated to prepare the compound represented by the formula (1). The elimination of the protecting group, i.e. silyl group can be realized by reaction in a solution of $Bu_4NF$ in THF or a solution of HF-pyridine in acetonitrile. An amount of the $Bu_4NF$ or HF-pyridine required for the elimination of the protecting group is sufficiently used, and the reaction is usually conducted at a reaction temperature within the range of 0° C. to 80° C.

The compound represented by the above formula (4) is a known compound and can be prepared from (S)-(+)-carvone through the following synthetic route according to the process described in, for example Journal of Organic Chemistry (J. Org. Chem.), 1989, 54, 4027.

The amounts of the compound represented by the above formula (1) and the compound represented by the above formula (4) to be used for the coupling reaction for the preparation of the compound represented by formula (2) are stoichiometrically equimolar; however, either one, usually a more readily available one is used in a small excess for surely completing the reaction.

A catalyst such as Pd(II) or Pd(0) can be employed as the palladium catalyst used for the coupling reaction. Pd(OAc)$_2$, PdCl$_2$(PhCN)$_2$, Pd(Ph$_3$P)$_2$Cl$_2$, Pd$_2$(dba)$_3$, Pd(Ph$_3$P)$_4$, Pd(dppe)$_2$ and the like are cited as typical examples of the catalyst.

The amount of the palladium catalyst to be used herein is within the range of is 0.5 to 100 mol %, preferably 1.0 to 30 mol % based on 1.0 mol of the compound represented by the above formula (1). In the process, the reaction may be carried out by adding a phosphorus compound such as triphenylphosphine or 1,2-bis(diphenylphosphino)ethane (dppe) for the purpose of preparing a more active Pd(0)-tertiary phosphine complex in the reaction system.

Examples of the additive to be used for the coupling reaction include triethylamine, diisopropylethylamine, pyridine, quinoline, lithium chloride and the like. The amount of the additive to be used is 1 to 20 equivalents, preferably 1 to 5 equivalents based on 1 equivalent of the palladium catalyst.

Examples of the reaction solvent include tetrahydrofuran, ethanol, dimethylformamide, dimethyl sulfoxide and the like. The amount of the solvent to be used is within the range of 1 to 500 mL, preferably 10 to 200 mL based on 1 g of the compound represented by the above formula (1). The reaction temperature used is usually within the range of room temperature to the boiling point of the solvent. The reaction time varies with the reaction solvent and reaction temperature to be used and is usually determined while monitoring the disappearance of the substrate and the formation of the objective substance by thin-layer chromatography, HPLC or the like. The reaction time, however, is usually about 1 to 30 hours.

The compound which is represented by the above formula (2) and prepared by the processes of the present invention can be derivatized into the compound represented by the above formula (3) by, if necessary, carrying out catalytic reduction or thermal isomerization.

The derivation of the compound represented by the above formula (2) into the compound represented by the above formula (3) is carried out by initially catalytically reducing the compound represented by the above formula (2). For example, reference can be made to known literature such as Shin Jikken Kagaku Koza (Vol. 15, Oxidation and Reduction, p. 425); J. Chem. Soc. (C), 1971, 2963; Tetrahedron, 47, 3485 or the like.

Specifically, the catalytic reduction is carried out by dissolving the compound represented by the above formula (2) in a solvent inert to the catalytic reduction, for example, a hydrocarbon solvent such as pentane, hexane or isooctane; an ether solvent such as diethyl ether or THF; or an alcoholic solvent such as MeOH or EtOH, adding a catalyst (a Lindlar catalyst is frequently used for selective reduction of a carbon-carbon triple bond into a carbon-carbon double bond) and, if necessary, a basic compound such as quinoline for the purpose of lowering the activity of the catalyst with hydrogen under atmospheric pressure or under pressure (use under an excessively high pressure is undesirable).

The amount of the catalyst to be used herein is 0.1 to 50 g, usually about 1.0 to 20 g based on 100 g of the substrate. The amount of the basic compound to be added is within the range of 0 to 50 g based on 1.0 g of the amount of the catalyst to be used. The reaction temperature to be used is usually within the range of room temperature to 40° C. Since the reaction time varies with the reaction solvent, reaction temperature and hydrogen pressure to be used, the reaction temperature is preferably determined while monitoring the stop of consumption of the hydrogen, disappearance of the substrate and the formation of the objective substance by HPLC.

Since the reduced product is frequently present as a mixture represented by the formula, the mixture is preferably thermally isomerized by heating to produce the objective compound represented by the above formula (3).

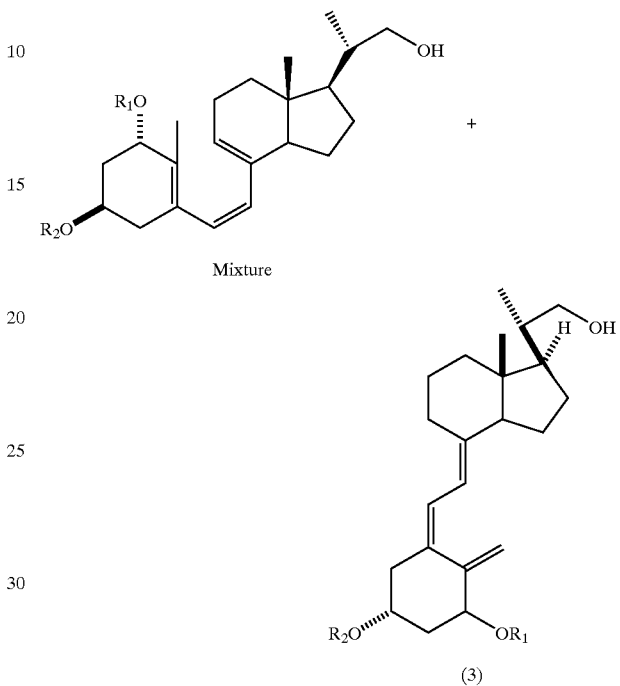

(3)

When the reaction temperature of the thermal isomerization herein is too low, there are problems that the thermal isomerization proceeds very slowly or does not proceed. On the other hand, when the reaction temperature is too high, there is a fear of causing the thermal decomposition of the isomerized compound. Thereby, the reaction temperature is within the range of 50 to 200° C., preferably 80 to 150° C. Although the mixture itself can directly be heated for the thermal isomerization, a solvent having the boiling point within the range of 80 to 150° C. is usually used. A hydrocarbon solvent such as isooctane is particularly preferable as the solvent; however, a solvent inert to the mixture can be used as the solvent for the thermal isomerization. The amount of the solvent to be used is within the range of 0 to 1000 mL, preferably 0 to 200 mL based on 1 g of the mixture. After completing the reduction reaction, the mixture can directly be heated; however, the mixture may be heated after separating the catalyst by filtration or the like. Otherwise, the solvent is distilled off, and the thermal isomerization may be carried out after distilling off the solvent and replacing the solvent with a different solvent. After purification by silica gel chromatography or the like, the purified product may be thermally isomerized.

The compound which is represented by the above formula (3) and prepared by the processes of the present invention can be derived into the compound represented by the above formula (5) by, if necessary, oxidizing the compound represented by the above formula (3).

The derivation of the compound represented by the above formula (3) into the compound represented by the above formula (5) can be carried out by using oxalyl chloride, DMSO or triethylamine as an oxidizing agent and using dichloromethane, toluene, acetone, acetonitrile or hexane as a reaction solvent by referring to known literature, for example, Shin Jikken Kagaku Koza (Vol. 15, Oxidation and Reduction, p. 802); J. Org. Chem., 1979, 44, 4148; J. Org. Chem., 1978, 43, 2480; and Synthesis, 1978, 297. Furthermore, the derivation can be realized by oxidation reaction under the so-called Swern oxidation reaction conditions or oxidation with $KMnO_4$, $MnO_2$, the Jones reagent, the Collins reagent, an oxidizing agent of an Ru catalyst and NMO (N-methylmorpholine N-oxide) in acetone solvent.

An example of preparing a 1α-hydroxyvitamin D derivative will be described hereinafter.

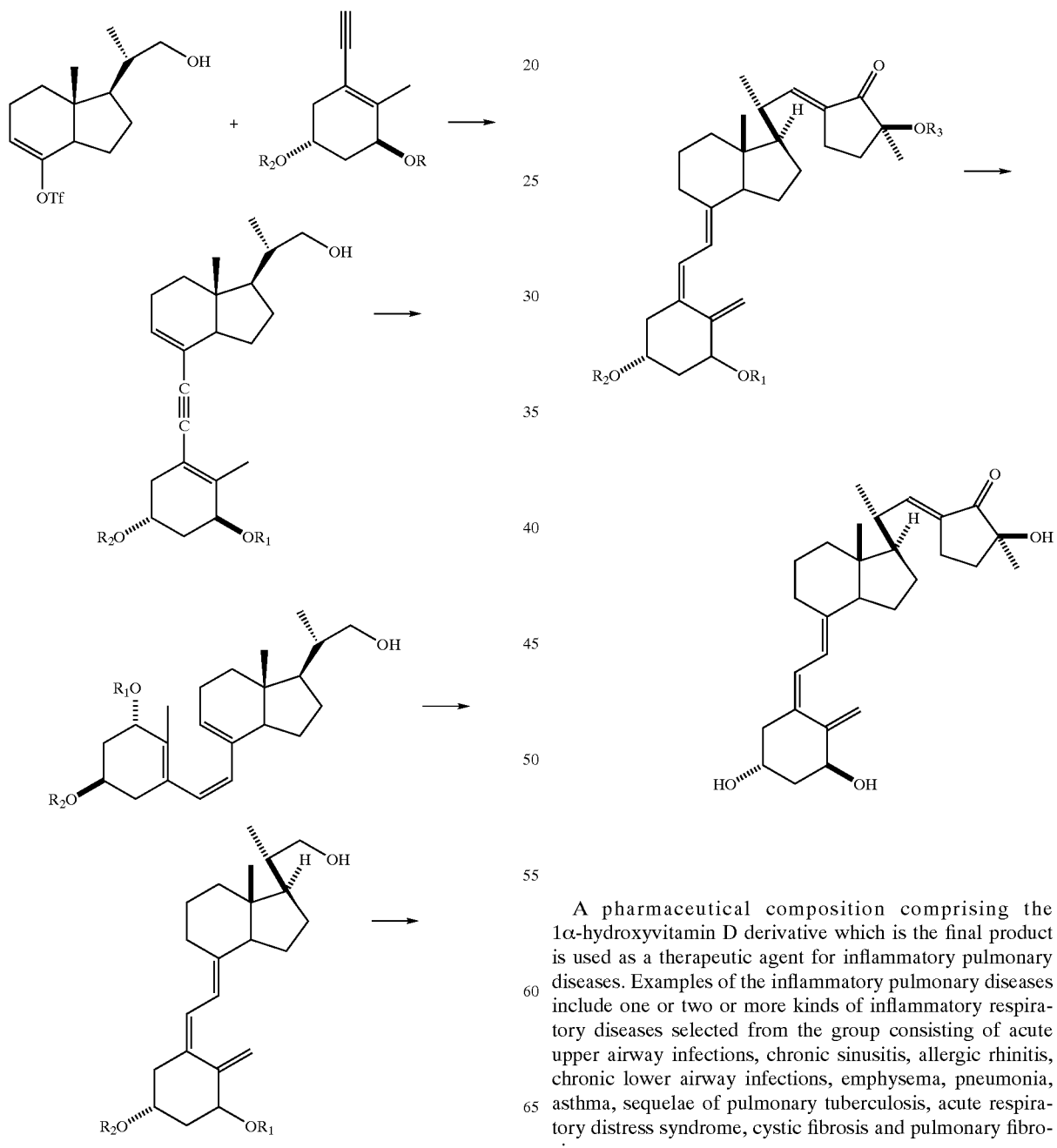

A pharmaceutical composition comprising the 1α-hydroxyvitamin D derivative which is the final product is used as a therapeutic agent for inflammatory pulmonary diseases. Examples of the inflammatory pulmonary diseases include one or two or more kinds of inflammatory respiratory diseases selected from the group consisting of acute upper airway infections, chronic sinusitis, allergic rhinitis, chronic lower airway infections, emphysema, pneumonia, asthma, sequelae of pulmonary tuberculosis, acute respiratory distress syndrome, cystic fibrosis and pulmonary fibrosis.

EXAMPLES

Example 1

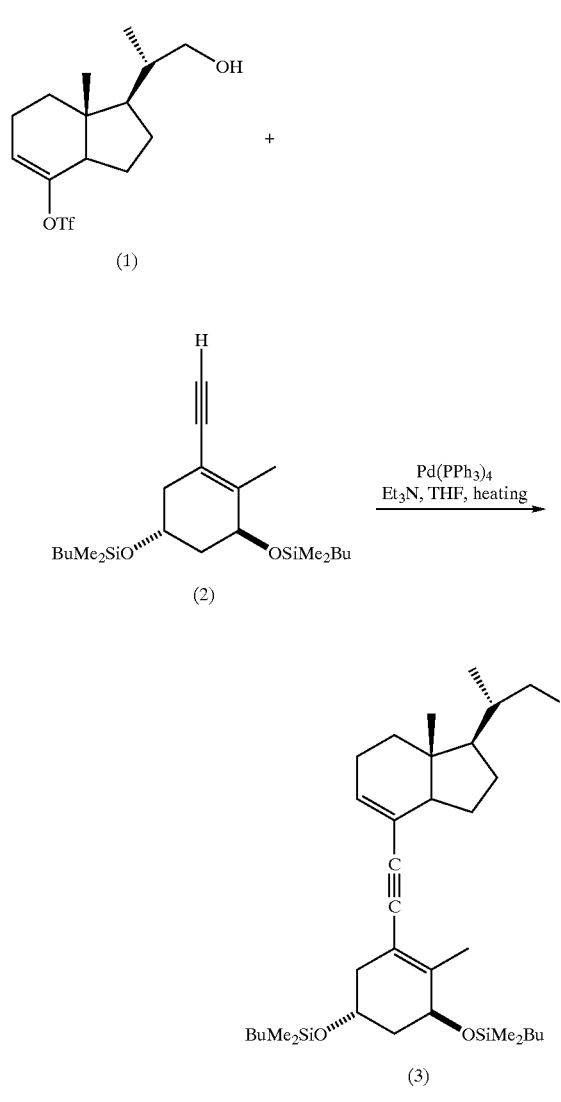

Example 2

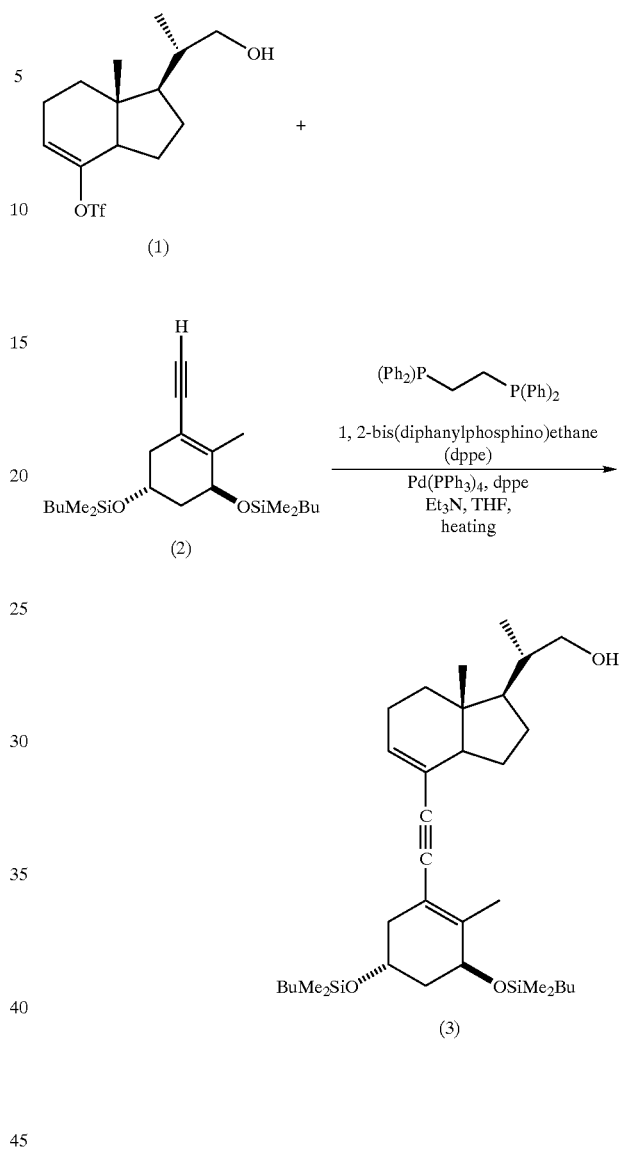

The enol triflate derivative (1) (0.685 g, 2.0 mmol) and the A-ring (2) compound 0.838 g, 2.2 mmol) were dissolved in THF (20 mL), and Pd(PPh$_3$)$_4$ (70 mg, 0.06 mmol) (a purified product obtained by recrystallizing a commercial available product with toluene solvent) was then added to the resulting solution. The mixture solution was stirred at room temperature for 10 minutes. Et$_3$N (0.836 mL, 6.0 mmol) was subsequently dropped, and the resulting mixture was stirred at 75° C. for 16 hours with heating. A saturated aqueous ammonium chloride was added to the reaction mixture, and ethyl acetate was further added to carry out extraction. The organic phase was washed with a saturated brine, then dried over anhydrous magnesium sulfate and concentrated. The resulting crude product was purified by silica gel column chromatography (hexane/ethyl acetate=5/1) to provide 1.03 g (90%) of the objective compound (3).

$^1$H-NMR (200 MHz) (CDCl$_3$, δ): 0.04 (s, 6H), 0.05 (s, 6H), 0.7 (s, 3H), 0.9 (s, 18H), 1.05 (d, 3H, J=8 Hz), 1.2–2.5 (m, 19H), 3.3–3.4 (m, 1H), 3.6–3.7 (m, 1H), 4.05–4.2 (m, 2H), 5.9–6.0 (d, 1H, J=2 Hz).

A flask was charged with Pd(PPh$_3$)$_4$ (70 mg, 0.06 mmol; 3.0 mol %), and THF (10 mL) was added. A solution of dppe (1,2-bis(diphenylphosphino)ethane) (52 mg, 0.13 mmol) in THF (5 mL) was then added to the flask, and the resulting mixture was stirred at room temperature for 10 minutes. A solution of the enol triflate derivative (1) (0.6847 g, 2.0 mmol) in THF (5 mL) was added to the flask, and the resulting mixture was stirred at room temperature for 10 minutes. The A-ring compound (2) was dissolved in THF (10 mL), and Et$_3$N (0.836 mL, 6.00 mmol) was added. The resulting mixture solution was then dropped into the flask and stirred at 75° C. for 16 hours with heating. A saturated aqueous ammonium chloride was added to the reaction mixture, and ethyl acetate was further added to carry out extraction. The organic phase was washed with a saturated brine, subsequently dried over anhydrous magnesium sulfate and concentrated. The resulting crude product was purified by silica gel column chromatography (hexane/ethyl acetate= 5/1) to afford 1.14 g (99%) of the objective compound (3).

Example 3

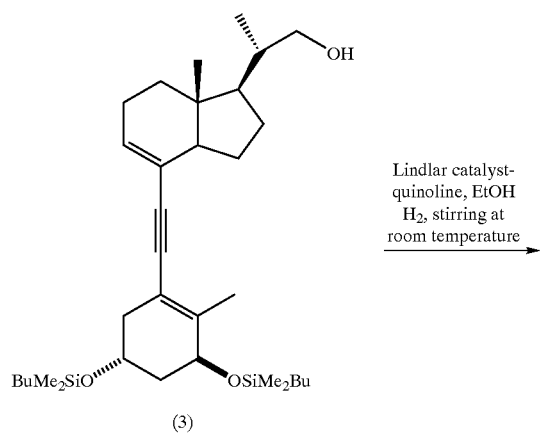

Example 4

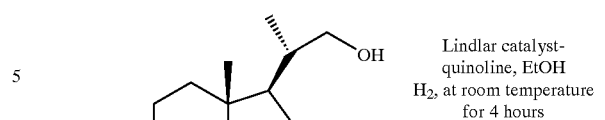
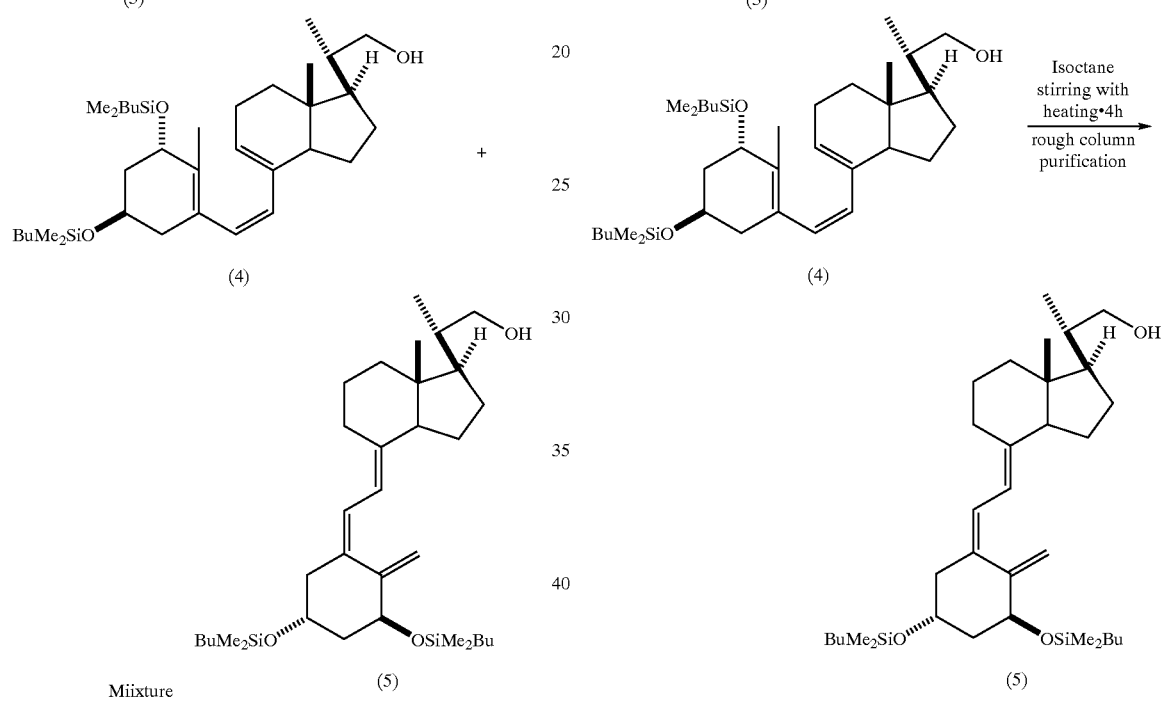

A Lindlar catalyst (80 mg) was suspended in ethanol (30 mL) and quinoline (0.10 mL) and activated with hydrogen gas. A solution of the coupling reaction product (3) (800 mg, 1.396 mmol) in ethanol (40 mL) was then added to the suspension of the Lindlar catalyst in the ethanol at room temperature, and the resulting mixture was stirred under a hydrogen gas atmosphere for 4 hours. The gas in the reaction vessel was replaced with nitrogen, and the catalyst was subsequently separated from the mixture by filtration. The obtained filtrate was concentrated to provide a residue (0.93 g). The concentrated residue was subjected to column purification (silica gel: Daiso Gel IR-60 No 1001 20 g, a packing solvent: hexane/ethyl acetate=4/1 and an eluent: hexane/ethyl acetate=4/1) to provide the product (0.720 g, 1.26 mmol, yield: 90%). As a result of NMR measurement, the resulting purified product was a mixture of the compound represented by the above formula (4) with the compound represented by the above formula (5).

The Lindlar catalyst (80 mg) was suspended in ethanol (30 mL) and quinoline (0.10 mL), and the resulting suspension was activated with hydrogen gas. A solution of the coupling reaction product (3) (800 mg, 1.396 mmol) in ethanol (40 mL) was added to the suspension of the Lindlar catalyst in the ethanol at room temperature, and the resulting mixture was stirred for 4 hours. The gas in the reaction vessel was replaced with nitrogen, and the catalyst was then separated from the mixture by filtration. The resulting filtrate was concentrated to afford a residue (0.931 g). Isooctane (50 mL) was added to the concentrated residue, and the mixture was stirred for 2 hours with heating. After allowing the mixture to cool, the cooled mixture was concentrated to provide a residue (0.932 g). The concentrated residue was subjected to column purification (silica gel: Daiso Gel IR-60 No 1001 20 g, a packing solvent: hexanelethyl acetate=4/1 and an eluent: hexane/ethyl acetate=4/1) to afford the objective compound (5) (0.619 g, 1.08 mmol, yield in two steps: 77%).

$^1$H-NMR (200 MHz) (CDCl$_3$, δ): 0.04 (s, 6H), 0.05 (s, 6H), 0.55 (s, 3H),0.9 (s, 18H), 1.05 (d, 3H, J=8 Hz), 1.2–2.1 (m, 14H), 2.1–2.2 (m, 1H), 2.35–2.5 (m, 1H), 2.7–2.9 (m,

2H), 3.2–3.4 (m, 1H), 4.05–4.2 (m, 1H), 4.3–4.4 (m, 1H), 4.85 (d, 1H, J=2 Hz), 5.2 (d, 1H, J=2 Hz), 5.2 (d, 1H, J=2Hz), 5.9–6.3 (d, 1H, J=14 Hz,), 6.15–6.25 (d, 1H, J=14 Hz,).

IR (KBr-disk): 3240 cm$^{-1}$ (νOH).

Example 5

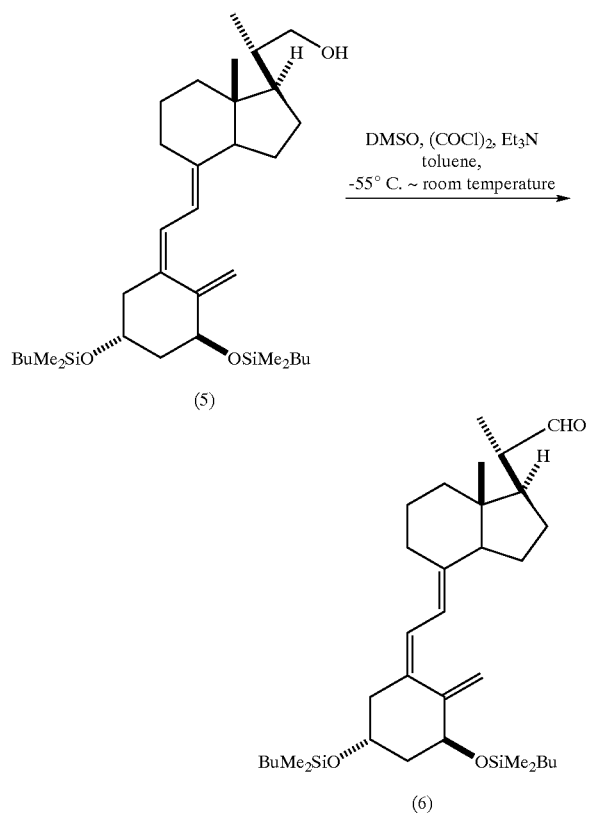

A flask was charged with oxalyl chloride (1.96 mL, 22.4 mmol), and toluene (150 mL) was added. The resulting mixture was cooled to −55° C. A solution of DMSO (3.19 mL, 44.9 mmol) in toluene (15 mL) was dropped into the mixture for 5 minutes, and the obtained mixture was stirred at −55° C. for 45 minutes. A solution of the hydroxymethyl derivative (5) (4.30 g, 7.48 mmol) in toluene (100 mL) was dropped into the flask for 10 minutes, and the resulting mixture was stirred at −55° C. for 60 minutes. Triethylamine (8.34 mL, 59.8 mmol) was added to the flask, and the resulting mixture was stirred at −55° C. for 10 minutes and further stirred at room temperature for 60 minutes. The reaction mixture was added to a saturated aqueous ammonium chloride (250 mL) to carry out extraction with ethyl acetate (250 mL). The organic layer was washed with a 1 mol/L aqueous solution of HCl (150 mL×2), a saturated aqueous solution of sodium hydrogencarbonate (150 mL×2) and a saturated brine (150 mL×2). The aqueous phase was extracted with ethyl acetate (150 mL). The organic phase was dried over anhydrous magnesium sulfate and concentrated. The resulting crude product (5.48 g) was subjected to column purification (silica gel: Daiso Gel IR-60 No 1001 117 g, a packing solvent: hexane/ethyl acetate=10/1 and an eluent: hexane/ethyl acetate=10/1) to provide the objective compound (6) (4.078 g, 7.12 mmol, yield: 95%).

$^1$H-NMR (200 MHz) (CDCl$_3$, δ): 0.04 (s, 6H), 0.05 (s, 6H), 0.55 (s, 3H), 0.85 (s, 18H), 1.15 (d, 3H, J=8 Hz), 1.2–2.9 (m, 16H), 4.05–4.25 (m, 2H), 4.3–4.4 (m, 1H), 4.85 (d, 1H, J=2 Hz), 5.15 (d, 1H, J=2 Hz), 5.95–6.10 (d, 1H, J=14 Hz,), 6.15–6.25 (d, 1H, J=14 Hz), 9.60(d, 1H, J=2 Hz,).

IR (KBr-disk): 1728 cm$^{-1}$ (νC═O).

Reference Example 1

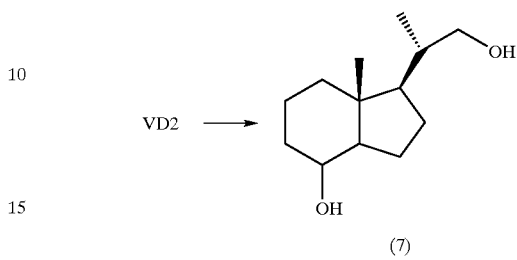

Vitamin D$_2$ (VD$_2$, 75.0 g, 189 mmol) was dissolved in methanol (4.5 L) under a nitrogen atmosphere, and the resulting solution was cooled to −78° C. Oxygen was passed through an ozonizer, and the generated ozone was bubbled into the methanol solution for 9 hours. Argon gas was further bubbled into the solution for 15 minutes, and 45 g of NaBH$_4$ was then added to stir the reaction mixture overnight. The methanol was distilled off under a reduced pressure, and 1 L of water was added to the resulting residue. Extraction with 2 L of ether was carried out three times, and the extracted ether solutions were washed with a saturated brine (1 L×2), dried over anhydrous magnesium sulfate and concentrated. The resulting crude product was subjected to column purification (silica gel: Daiso Gel IR-60 No 1001 1.0 kg, a packing solvent: hexane/ethyl acetate=3/1 and an eluent: hexane/ethyl acetate=3/1 to 2/3) to afford the objective compound (7) (30.45 g, 144 mmol, yield: 76%).

$^1$H-NMR (200 MHz) (CDCl$_3$, δ): 0.95 (s, 3H), 1.05 (d. 3H, J=8 Hz), 1.1–2.1 (m, 15H), 3.3–3.4 (m, 1H), 3.6–3.7 (m, 1H), 4.1 (b.s, 1H).

Example 6

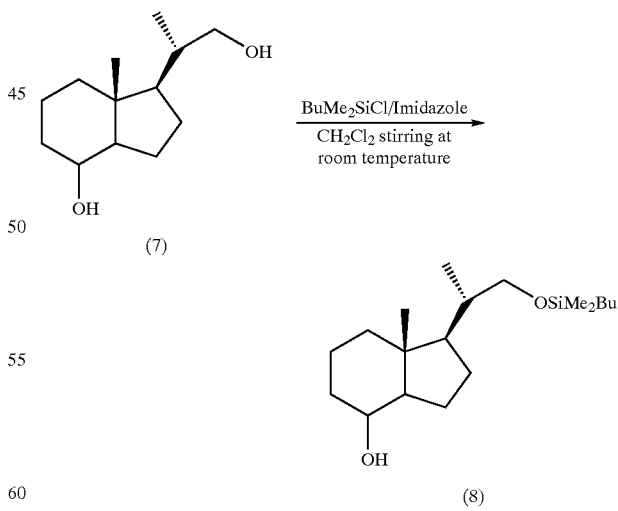

The diol derivative (7) (26.54 g, 125 mmol) was dissolved in dichloromethane (375 mL) in a flask, and imidazole (19.97 g, 293.3 mmol) was added. The resulting mixture was cooled to 0° C., and t.BuMe$_2$SiCl (22.675 g, 150 mmol) was added. The obtained mixture was stirred at 0° C. for 10 minutes and then at room temperature for 2 hours. To the reaction mixture, was added 500 mL of water. The obtained mixture was separated with 500 mL of ethyl acetate. Extraction was carried out, and the aqueous phase was extracted with 250 mL of ethyl acetate. The organic phase was washed with 500 mL of water and a saturated brine (500 mL×2), dried over anhydrous magnesium sulfate and concentrated. The resulting crude product (weight of the crude substance 47.36 g) was subjected to column purification (silica gel: Daiso Gel IR-60 No 1001 1.0 kg, a packing solvent: hexane/ethyl acetate=10/1 and an eluent: hexane/ethyl acetate=10/1) to provide the objective compound (8) (39.81 g, 121.9 mmol, yield: 98%).

$^1$H-NMR (200 MHz) (CDCl$_3$, δ): 0.02 (s, 6H), 0.9 (s, 3H), 0.95 (s, 9H), 0.95 (d, 3H, J=8 Hz), 1.1–2.1 (m, 14H), 3.2–3.3 (m, 1H), 3.5–3.6 (m, 1H), 4.1 (b.s, 1H).

Example 7

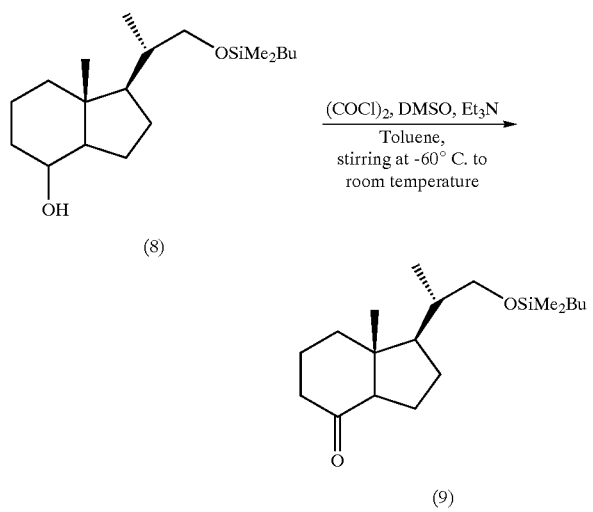

A solution of oxalyl chloride (14.20 mL, 200 mmol) in toluene (20 mL) was dropped into a flask for 5 minutes, and the solution was then stirred at −55° C. for 45 minutes. A solution of the monosilyl ether derivative (8) (16.33 g, 50.0 mmol) in toluene (200 mL) was dropped into the flask for 10 minutes, and the resulting mixture was stirred at −55° C. for 50 minutes. Triethylamine (35 mL, 250.0 mmol) was added, and the resulting mixture was stirred at −55° C. for 30 minutes and then at room temperature for 90 minutes. The reaction mixture was added to a saturated aqueous ammonium chloride (1000 mL) to carry out extraction with ethyl acetate (500 mL). The organic phase was washed with a 1 mol/L aqueous solution of HCl (500 mL×2), a saturated aqueous solution of sodium hydrogencarbonate (500 mL×2) and a saturated brine (500 mL×2), and the aqueous phase was extracted with ethyl acetate (250 mL). The resulting organic phase were dried over anhydrous magnesium sulfate and concentrated. The obtained crude product (weight of the crude substance 21.42 g) was subjected to column purification (silica gel: Daiso Gel IR-60 No 1001 430 g, a packing solvent: hexane/ethyl acetate=10/1 and an eluent: hexane/ethyl acetate=10/1) to afford the objective compound (9) (15.50 g, 47.76 mmol, yield: 95.5%).

$^1$H-NMR(200 MHz) (CDCl$_3$, δ): 0.02 (s, 6H), 0.6 (s, 3H), 0.9 (s, 9H), 1.0 (d,3H, J=8 Hz), 1.3–2.5 (m, 13H), 3.2–3.4 (m, 1H), 3.5–3.6 (m, 1H).

IR (KBr-disk): 17170 cm$^{-1}$ (νC=O).

Example 8

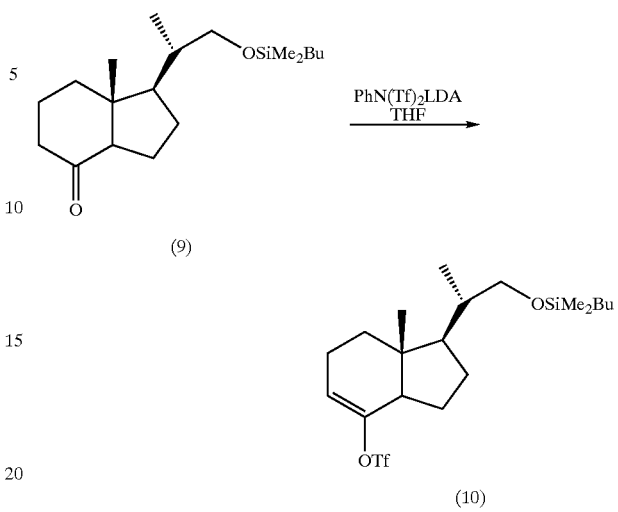

A flask was charged with diisopropylamine (9.11 mL, 65.0 mmol) and distilled THF (100 mL), and n-BuLi (60.0 mmol) was then dropped while stirring the mixture under cooling with ice. The resulting mixture was stirred under cooling with ice for 30 minutes. The ketosilyl ether derivative (9) (16.23 g, 50.0 mmol) was dissolved in THF (125 mL) and cooled with ice. The solution of the LDA in the THF was dropped. The resulting mixture was stirred at room temperature for 60 minutes. The obtained mixture was cooled again with ice and stirred. A solution of PhN(Tf)$_2$ (19.65 g, 55.0 mmol) in THF (125 mL) was dropped, and the resulting mixture was stirred at room temperature for 2 hours. The reaction mixture was added to a saturated aqueous solution of ammonium chloride, and the obtained mixture was separated with hexane and extracted. The aqueous phase was extracted with 350 mL of hexane, and the extracted hexane solution was washed with 350 mL of a saturated brine 2 times. The resulting organic phase were dried over anhydrous magnesium sulfate and concentrated. The obtained crude product was purified by silica gel column chromatography (hexane/ethyl acetate=10/1) to provide the objective compound (10) (19.90 g, 43.6 mmol, yield: 87%).

$^1$H-NMR (200 MHz) (CDCl$_3$, δ): 0.02 (s, 6H), 0.8 (s, 3H), 0.9 (s, 9H), 1.0 (d, 3H, J=8 Hz), 1.3–2.1 (m, 8H), 2.2–2.4 (m, 2H), 2.4–2.6 (m, 1H), 3.3–3.4 (m, 1H), 3.5–3.6 (m, 1H), 5.6 (d.d, 1H, J=2 Hz).

IR (KBr-disk): 1678 cm$^{-1}$ (νC=C).

Example 9

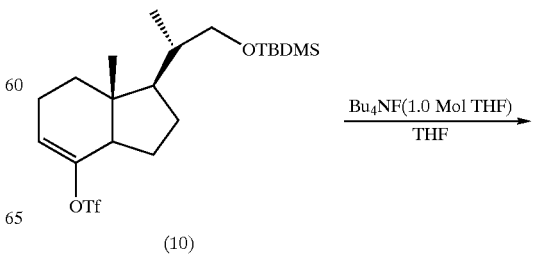

-continued

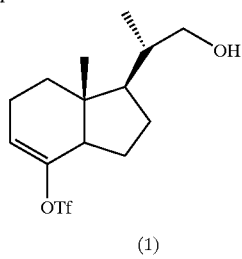

(1)

The silyl enol triflate derivative (10) (4.566 g 10.0 mmol) was dissolved in THF (20.0 mL), and Bu$_4$NF (1.0 M THF solution) (15.0 mL. 15.0 mmol) was dropped while stirring the solution at room temperature. The resulting mixture was then stirred at room temperature for 4 hours. The reaction mixture was added to a saturated aqueous solution of ammonium chloride, and the obtained mixture was extracted with ethyl acetate. The organic phase was washed with water, and the resulting organic phase was dried over anhydrous magnesium sulfate and concentrated. The obtained crude product was purified by silica gel column chromatography (hexane/ethyl acetate=2/1) to afford the objective compound (1) (3.085 g, 9.0 mmol, yield: 90%).

$^1$H-NMR (200 MHz) (CDCl$_3$, δ): 0.8 (s, 3H), 1.1 (d, 3H, J=8 Hz), 1.2–1.9 (m, 7H), 1.9–2.1 (m, 2H), 2.2–2.4 (m, 2H), 2.4–2.6 (m, 1H), 3.3–3.5 (m, 1H), 3.6–3.7 (m, 1H), 5.6 (d.d, 1H, J=2 Hz).

IR (KBr-disk): 3300 cm$^{-1}$ (νOH), 1678 cm$^{-1}$ (νC=C).

What is claimed is:

1. A compound represented by the formula (1):

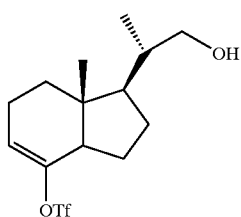

(1)

wherein, Tf represents SO$_2$CF$_3$.

2. A compound represented by the formula (2):

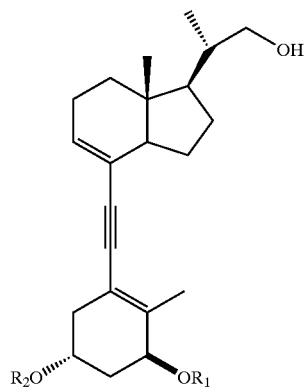

(2)

wherein, R$_1$ and R$_2$ are each the same or different and represent each a hydrogen atom, a tri(C$_1$–C$_7$ hydrocarbon)silyl group, a diphenyl(C$_1$–C$_7$ hydrocarbon)silyl group or a group forming an acetal bond or an ester bond with an oxygen atom to which each of R$_1$ and R$_2$ is bound.

3. A process for the preparation of the compound represented by the formula (2):

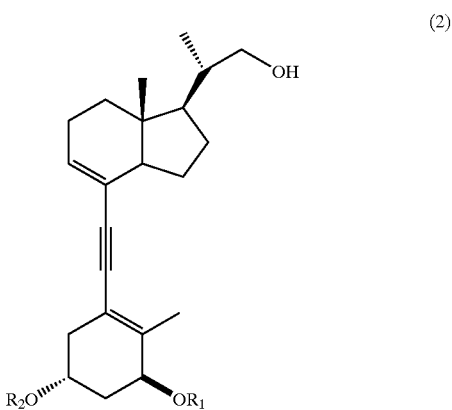

(2)

wherein, R$_1$ and R$_2$ are each the same as in the formula (4), comprising the step of reacting a compound represented by the formula (1):

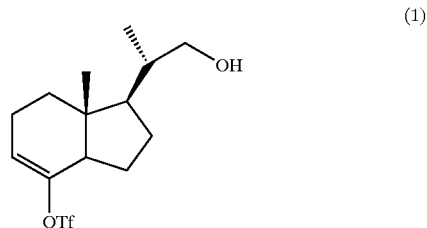

(1)

wherein, Tf represents SO$_2$CF$_3$, with a compound represented by the formula (4):

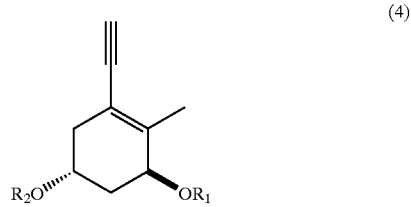

(4)

wherein, R$_1$ and R$_2$ are each the same or different and represent each a hydrogen atom, a tri(C$_1$–C$_7$ hydrocarbon)silyl group, a diphenyl(C$_1$–C$_7$ hydrocarbon)silyl group or a group forming an acetal bond or an ester bond with an oxygen atom to which each of R$_1$ and R$_2$ is bound, in the presence of a palladium catalyst and an additive.

4. A process for the preparation of the compound represented by the formula (3):

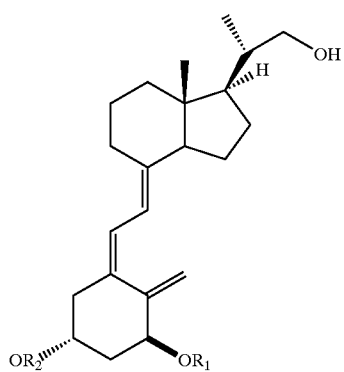

(3)

wherein, $R_1$ and $R_2$ are each the same as in the formula (2), comprising the steps of;

a) catalytically reducing the compound represented by the formula (2):

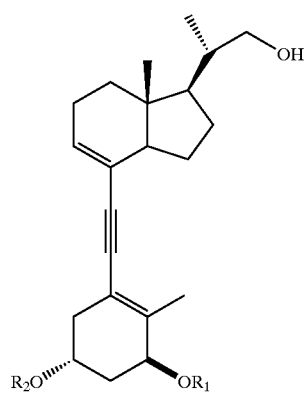

(2)

wherein, $R_1$ and $R_2$ are each the same or different and represent each a hydrogen atom, a tri($C_1$–$C_7$ hydrocarbon)silyl group, a diphenyl($C_1$–$C_7$ hydrocarbon)silyl group or a group forming an acetal bond or an ester bond with an oxygen atom to which each of $R_1$ and $R_2$ is bound, in the presence of a Lindlar catalyst and hydrogen gas and
    b) heating the obtained product.

\* \* \* \* \*